United States Patent [19]

Perrault et al.

[11] Patent Number: 4,717,378
[45] Date of Patent: Jan. 5, 1988

[54] METHODS FOR DETECTING DEHYDRATION OF A BIOMEDICAL HYDROGEL

[75] Inventors: James J. Perrault, Brooklyn Center, Minn.; George Jordan, Fairfield, Conn.

[73] Assignee: Medtronic, Inc., Minneapolis, Minn.

[21] Appl. No.: 846,387

[22] Filed: Mar. 31, 1986

[51] Int. Cl.⁴ ............................................. A61N 1/30
[52] U.S. Cl. ...................................... 604/20; 128/639; 128/660; 128/803; 604/111; 604/404
[58] Field of Search ................... 128/639–641, 128/798, 802, 803, 303.13, 660; 604/20, 111, 404, 318

[56] References Cited

U.S. PATENT DOCUMENTS

| | | | |
|---|---|---|---|
| 3,989,050 | 11/1976 | Buchalter | 128/803 X |
| 4,391,278 | 7/1983 | Cahalan et al. | 128/640 |
| 4,593,053 | 6/1986 | Jevne et al. | 523/111 |

*Primary Examiner*—Lee S. Cohen
*Attorney, Agent, or Firm*—Grady J. Frenchick; John L. Rooney; Joseph F. Breimayer

[57] ABSTRACT

A visual (as opposed to mechanical or electronic) method for detecting the state of dehydration (or hydration) of a biomedical hydrogel is disclosed. The method contemplates incorporating a pH sensitive indicator into the hydrogel as it is prepared and applying the hydrogel to the skin-contacting surface of a biomedical device such as an electrode. Shortly before the biomedical device is to be used, the color of the hydrogel on the device is visually compared with its freshly-prepared color to determine the approximate state of dehydration of the gel.

10 Claims, No Drawings

METHODS FOR DETECTING DEHYDRATION OF A BIOMEDICAL HYDROGEL

DESCRIPTION OF THE INVENTION

This invention relates to methods for detecting a state of relative dehydration, hydration or "dry out" in biomedical polymers. More particularly, this invention relates to methods for visually identifying whether a polymeric, preferably conductive, hydrogel or gel has lost certain desirable characteristics, such as conductivity or transmissivity to sound, as a result of loss of water.

BACKGROUND OF THE INVENTION

Biomedical polymers, hydrogels or gels are a relatively recent development which has had a substantial impact on the biomedical technology. These synthetic, polymeric materials have been used at the interface between various biomedical devices, e.g., electrocardiogram (ECG) electrodes, TENS electrodes, electrosurgery return pads, iontophoresis electrodes, ultrasound electrodes, wound dressings or coverings and skin or surface of an organ. They have largely supplanted naturally-occurring polymers such as karaya gum and guar which were the biomedical materials of choice before development of synethetic hydrogels. As has been described in the literature, synthetic biomedical polymers are a significant advance over their naturally-occurring counterparts in that the properties of the synthetic materials are more controllable, less expensive and more uniform. Given that these materials are used in medical and biomedical applications, the importance of controllability and uniformity of their properties is readily apparent.

Synthetic biopolymers, such as conductive, polymeric hydrogels or gels, do have one significant drawback in that upon storage, these materials tend to lose some of their water content (i.e., they tend to dehydrate or "dry out"). Since these materials normally conduct electricity city (and in some cases, sound), the loss of water tends to adversely effect a very important characteristic. Prior to this invention, there was no easy way for the user of a biomedical device having a polymeric hydrogel in a working surface or skin-contacting surface thereof to tell whether the hydrogel had been dehydrated to the point of significantly altering its properties (e.g., conductivity) short of applying the biomedical device to the patient and testing it. This invention provides an easy, visual method for detecting whether biomedical gels or hydrogels have lost an excessive amount of water so as to reduce their conductivity (to electricity or sound) and stability so as to not be suitable for the purpose intended.

BRIEF SUMMARY OF THE INVENTION

Briefly, in one aspect, this invention is a visual method for detecting a state of relative dehydration (or hydration) of a gel on a skin contacting or working surface of a biomedical device comprising the steps of selecting a weakly acid or a weakly basic, pH sensitive indicator; preparing the gel by incorporating the selected indicator therein, thereby producing a gel having a first color indicating adequate hydration; applying the colored gel to a working or skin-contacting surface of the biomedical device; and shortly before using the biomedical device, visually comparing the color of the gel shortly before application with its first prepared color to determine the state of hydration of the gel.

In a preferred practice of this invention, the gel is prepared by mixing the indicator with the other raw materials, e.g., polymer powders, used to produce the polymeric gel prior to subsequent processing. It is within the contemplation of the invention that the indicator could be mixed with already polymerized gel.

In another preferred practice, a portion of the gel is covered, e.g., with a piece of transparent film which restricts the evaporation of water from the covered portion of the gel. The covered portion of the gel is then compared with the uncovered gel shortly before using the biomedical device. The covered gel tends to remain adequately hydrated, thus providing a good comparison "patch" or test area for comparison with uncovered electrode gel when hydration (or dehydration) state is later examined.

Preferred indicators are any skin-contact grade coloring having the requisite chemical characteristics specifically including sensitivity to changes in pH. Such preferred indicators are generally selected from the group consisting of Food, Drug and Cosmetic (FD&C) Blue #1, FD&C Blue #2, FD&C Green #3, D&C Green #8 or D&C Red #27.

"Biomedical device" as the term is used herein, is to be very broadly construed to mean essentially any device which is attached to the skin of a patient. Wound dressings, large area bandages and ultrasound interface pads, as well as TENS electrodes, ECG electrodes and iontophoresis devices are specifically contemplated.

"Working surface" or "skin-contacting surface", as the term is used herein, is intended to mean that portion (or the entirety) of a biomedical device which is adhered to the skin or the surface of an organ by means of a polymeric adhesive or biomedical adhesive.

"Biomedical polymer", as the term is used herein, is intended to mean essentially any water-containing, preferably conductive, preferably polymeric, material used to fix a biomedical device to a patient's skin or to the surface of an organ for the purpose of monitoring or controlling biological or electrical phenomenon.

Compositions with which the present invention may be employed are generally any hydrogel composition where the presence (or absence) of a given quantity or concentration of water is important to the gels' characteristics. U.S. Pat. No. 4,391,278 to Cahalan et al, the teaching of which is incorporated by reference herein, describes an acrylate-based material, viz., 2-acrylamido-2-methylpropanesulfonic acid (or its salts) which would be particularly useful as the gel material for the practice of this invention.

Canadian Pat. No. 1,181,582, the teaching of which is incorporated by reference herein, describes another electrically conductive adhesive comprised of an interpenetrating copolymer network of a stated composition, humectant and water. The hydrogel composition of this Canadian patent also would be useful in the practice of this invention.

Another preferred gel composition useful in the practice of the present invention is described in commonly owned, pending U.S. patent application Ser. No. 679,653, now U.S. Pat. No. 4,593,053, "Hydrophilic Pressure Sensitive Biomedical Adhesive Composition" in the name of Allan H. Jevne, Brett R. Vegoe, Carolann M. Holmblad and Patrick T. Cahalan. The '653 patent application discloses a skin-compatible, hydrophilic adhesive composition comprising 25 to 50 weight percent polyvinyl pyrolidone (PVP) having a molecular weight in the range of 100,000 to 600,000, 2 to 5 weight percent polyvinyl alcohol (PVA) having a molecular weight in the range of 150,000 to 300,000; 5 to 50 weight percent polar plasticizer; 3 to 50 weight percent water and 0 to 50 weight percent of an ionic or nonionic species. PVA/PVP gels are a particularly preferred class of gels useful in this invention.

"Gels" or "hydrogels" (including salts) are a preferred class of biomedical polymers. Preferred gels use sodium acetate s the electrolyte.

"Conductive", as the term is used herein, is generally intended to mean a biomedical polymer having a conductivity in the range of $1.0 \times 10^{-3}$ ohms$^{-1}$–cm$^{-1}$ to $1.0 \times 10^{-5}$ ohm$^{-1}$–cm$^{-1}$, preferably in the range of $1.0 \times 10^{-3}$ ohm$^{-1}$–cm$^{-1}$ to $1.0 \times 10^{-4}$ ohm$^{-1}$–cm$^{-1}$.

DETAILED DESCRIPTION OF THE INVENTION

The chemical principles which underlie this invention are well known. They are Le Chatelier's Principle and the chemistry of indicators. La Chatelier's Principle states that if an external stress is applied to a system at chemical equilibrium, then the equilibrium characteristics of the system will change so as to minimize the effect of that stress. The second principle on which this invention operates is that certain chemical species identifiably and predictably change color as the acidity or basicity (i.e., the pH) of their surrounding chemical environment changes. These chromatophoric (i.e., color absorbing) species are referred to as indicators since they permit a chemist to monitor the pH (i.e., its surrounding acidity or basicity expressed as—log [concentration] of H+) of a system merely by comparing its color with a standard. Perhaps the best known indicator (and one which would clearly operate in this invention) is phenolphthalein. Phenolphthalein changes from essentially colorless at a pH of 7 to intensely pink at a pH of 9. Simply stated, as the water content of the hydrogel decreases, its pH changes and, in turn, the color of the indicator also changes.

For example, many FD&C dyes fade or change color when placed in alkali solutions. In the case of sodium acetate gels, the pH is approximately 7, i.e., essentially neutral. As the gel dries out, water is lost from the system. According to Le Chatelier's Principle, when a system is subjected to a stress, its shifts toward a new equilibrium condition in such a way to relieve the stress. Sodium acetate gels react to the loss of water in such a way that they become more alkaline, which causes the FD&C dye to change color, e.g., from blue to colorless. Because sodium acetate is the salt of a strong base and a weak acid, the pH in an aqueous solution tends to be more basic. If the salt used in this gel were sodium chloride, the pH in an aqueous solution would be neutral because sodium chloride is the salt of a strong acid and a strong base. Therefore, it is highly probable that any gel made with the salt of a strong base and a weak acid would evidence a color change if an appropriate FD&C dye were mixed with it.

It is within the contemplation of this invention that a mixture of indicators or a mixture of an indicator (or indicators) and a colored, pH stable non-indicator would be employed. In this embodiment, for example, a mixture of the indicator FD&C Blue #1 and the highly colored non-indicator FD&C Red #3 could be employed. FD&C Blue #1 changes from intensely blue to colorless as the pH of the surrounding gel changes. FD&C Red #3, not being an indicator, does not change color as the pH of the gel changes. Thus a gel incorporating such a mixture would change from blue to red as it dehydrates.

This embodiment of the invention also illustrates one of the possible meanings of the term "first color" as used in this invention and in the attached claims. "First color" could mean essentially colorless, i.e., imparting no color to the gel.

When making a sodium acetate gel, the raw materials are weighed and placed in a heat controllable, stirrable reactor. The reactor is heated to 200° F., and the materials are poured into the reactor one by one. The particular order of addition is not critical. The first material to be added is deionized water; the last is polyvinyl pyrolidone, preferably having a molecular weight of 100,000 to 600,000. Sodium acetate (NaAc) and polyvinyl alcohol, preferably having a molecular weight of 150,000 to 300,000 should be added second to the last for convenience of mixing. After adding all materials except PVP, begin stirring at 100 rpm. Once the heat in the reactor has reached 200° F., PVP should be added. After adding PVP, the heat should be turned up to 250° F. At this point, the indicator selected could be added. Generally about 0.01 to 0.1 weight percent of indicator would be added to the mixture. Once the temperature reaches 250° F., the gel is stirred for another 2 hours. After heating for 2 hours, the stirring is reduced to 60 rpm, the heat is reduced to 200° F. and the gel is degassed by permitting it to cool while sealed. After the heat decreases to 200° F., the gel is ready to be extruded or formed to the particular application.

| Typical Compositions | |
| --- | --- |
| 1 | % |
| Glycerin | 22 |
| D.I. H$_2$O | 35 |
| Sodium Acetate | 8 |
| PVA (du Pont) | 4 |
| PVP (GAF) | 31 |
| P.E.G. | 15 |
| D.I. H$_2$O | 34 |
| NaAc | 7 |
| PVA | 4 |
| Sorbitol | 5 |
| PVP | 36 |
| PVA | 4 |
| PVP | 35 |
| Sorbitol | 4 |
| P.E.G. | 10 |
| D.I. H$_2$O | 40 |
| KCl | 5 |
| NaAc | 2 |

Utilization of the above typical compositions in the synthesis procedure produces a hydrogel of a given water content or hydration which has a first color, e.g., blue. This first color is the one that would obtained at the point when the gel is in its state of optimum or highest water content generally when it is first prepared. At this point, the hydrogel would likely have its greatest conductivity if, for example, the water content of the material were adjusted to enhance conductivity. If other hydration-dependent characteristics were of concern, then the water content of the particular material would be adjusted accordingly.

Subsequent to the above synthesis, the now colored hydrogel would be placed on the skin-contacting or working surface of the particular biomedical device chosen. Thus, for example, the hydrogel could be formed to be the size of an electrocardiogram (ECG) electrode. The electrode, with its colored hydrogel on the skin-contacting surface thereof, would then be packaged and shipped. The ultimate recipient of the ECG electrode would likely have stored the device in inventory for at least a short period of time thereby potentially exposing the gel to the possibility of dehydration or drying out. In the case of an ECG electrode, this would mean that its electrical conductivity characteristics would be dramatically reduced. When it becomes time for the ECG electrode to be used, all that it is necessary is for the user to visually check the color of the hydrogel on the ECG electrode with its color shortly after first preparation. If the color of the hydrogel at time of use is red as opposed to blue, then the hydrogel material has become dehydrated, and the electrode should not be used. Using this is expedient, the user avoids the potential waste of time and embarrassment of utilizing the biomedical device such as by placing it on the patient's body only to find that the electrical characteristics of the gel are such that the electrode is unusable. Thus in the practice of this invention, wasting of time and embarrassment are avoided.

The invention contemplates a visual comparison between the color of the hydrogel at time of application with its freshly prepared color. The particular manner in which this comparison is made is not critical to this invention. However, a preferred method of comparison has been developed which is particularly applicable to electrosurgery return electrodes. This preferred method contemplates the application of a small transparent piece of water impenetrable tape to a portion of the hydrogel after it is placed on the working surface of the electrode. This water impenetrable transparent tape contains the local state of hydration of the gel beneath it. In this manner a fairly-accurate, visually-comparable sample of the freshly prepared gel is maintained in close proximity to the rest of the hydrogel on the biomedical device.

Alternative means of making the comparison could include a colored picture of the freshly-prepared colored gel which would permit comparison prior to placement of the electrode on the patient's skin. This technique is comparable to that used with pH papers in which the acidity (or basicity) of a material is determined by comparing the pH paper color after testing with a standard color chart. With this teaching in mind, many modifications of the comparison step would be readily apparent to one of ordinary skill in this art.

This invention has been described, in detail, with particular reference to certain preferred embodiments as set forth above. It is to be understood that variations and modifications can be effected within the spirit and scope of this invention.

What is claimed is:

1. A visual method for detecting the state of dehydration of a polymeric gel disposed on the skin-contacting surface of a biomedical device comprising the steps of:
   selecting a weakly acidic or weakly basic, pH sensitive colored indicator;
   preparing the gel by incorporating the selected indicator therein to produce a gel having a first color;
   applying the first color gel to a skin-contacting surface of a biomedical device; and
   shortly before the device is to be used, visually comparing the color of the gel just before used with its first color to determine the relative state of dehydration of the gel.

2. A method according to claim 1 wherein the gel is prepared by the steps of mixing the selected indicator with the gel raw materials.

3. A method according to claim 1 wherein after the first color gel is applied to the skin-contacting surface of the biomedical device a visually transparent humidity barrier is placed on a portion of the gel, and the visual comparison is between a covered and uncovered portion of the gel.

4. A method according to claim 1 wherein the gel has sodium acetate as an electrolyte.

5. A method according to claim 1 wherein the indicator is selected from the group consisting of FD&C Blue #1, FD&C Blue #2, FD&C Green #3, D&C Green #8 or D&C Red #27.

6. A method according to claim 1 wherein the biomedical device is an iontophoresis electrode.

7. A visual method for detecting the state of dehydration of a conductive polymeric hydrogel disposed on the skin-contacting surface of a biomedical device comprising the steps of:
   selecting a weakly acidic or weakly basic pH sensitive colored indicator selected from the group consisting of FD&C Blue #1, FD&C Blue #2, D&C Green #3, D&C Green #8 or D&C Red #27;
   preparing the hydrogel by incorporating the selected indicator therein thereby producing a hydrogel having a first color;
   applying the first color hydrogel to a skin-contacting surface of the biomedical device; and
   shortly before the device is to be used, visually comparing the color of the hydrogel just before use with its first color to determine the relative state of dehydration of the gel.

8. A method according to claim 7 wherein the hydrogel is prepared by the steps of mixing the selected indicator with the gel raw materials.

9. A method according to claim 7 wherein after the first color gel is applied to the skin-contacting surface of the biomedical device a visually transparent barrier having a low moisture vapor transmission rate is placed on a portion of the gel, and the visual comparison is between a covered and uncovered portion of the gel.

10. A method according to claim 7 wherein the gel comprises sodium acetate.

* * * * *